US010976297B2

(12) United States Patent
Lock et al.

(10) Patent No.: US 10,976,297 B2
(45) Date of Patent: Apr. 13, 2021

(54) GRAPHENE-BASED PPB LEVEL SULFUR DETECTOR IN FUELS

(71) Applicant: The Government of the United States of America, as represented by the Secretary of the Navy, Arlington, VA (US)

(72) Inventors: Evgeniya H. Lock, Annandale, VA (US); F. Keith Perkins, Alexandria, VA (US); Anthony K. Boyd, Arlington, VA (US); Rachael L. Myers-Ward, Springfield, VA (US); David Kurt Gaskill, Alexandria, VA (US); Anindya Nath, Fairfax, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 256 days.

(21) Appl. No.: 16/012,849

(22) Filed: Jun. 20, 2018

(65) Prior Publication Data
US 2019/0107524 A1 Apr. 11, 2019

Related U.S. Application Data

(60) Provisional application No. 62/522,257, filed on Jun. 20, 2017.

(51) Int. Cl.
*G01N 27/12* (2006.01)
*G01N 33/00* (2006.01)
(Continued)

(52) U.S. Cl.
CPC ......... *G01N 33/287* (2013.01); *G01N 27/127* (2013.01); *G01N 33/00* (2013.01); *G01N 33/0044* (2013.01); *G01N 33/22* (2013.01)

(58) Field of Classification Search
CPC ........ G01N 27/12; G01N 33/00; G01N 33/22; G01N 33/28
(Continued)

(56) References Cited

U.S. PATENT DOCUMENTS 8,920,764 B2 * 12/2014 Star ..................... G01N 27/127
423/448
2010/0028559 A1 * 2/2010 Yan ....................... H01F 1/0054
427/558
(Continued)

OTHER PUBLICATIONS

Pham, V. H. et al, Carbon 2010, 48, 1945-1951.*
(Continued)

*Primary Examiner* — Arlen Soderquist
(74) *Attorney, Agent, or Firm* — US Naval Research Laboratory; Rebecca Forman

(57) ABSTRACT

A sensitive and selective, in-line method to measure and validate the sulfur content at ppb levels in both the liquid and gas phase of fuel. The method includes etching graphene, for example to form a mesa structure comprising horizontal or vertical lines or an array of multidentate star features; functionalizing the etched graphene and attaching metal oxide nanoparticles to the functionalized graphene to form a device; exposing the device to a fuel in the gas or liquid phase; detecting a change in conductivity when sulfur is present in the fuel; and recovering the device for future use. Also disclosed is the related in-line graphene-based ppb level sulfur detector for fuels.

12 Claims, 17 Drawing Sheets

(51) Int. Cl.
*G01N 33/22* (2006.01)
*G01N 33/28* (2006.01)

(58) Field of Classification Search
USPC .................................................. 436/119–120
See application file for complete search history.

(56) References Cited

U.S. PATENT DOCUMENTS

| | | | | |
|---|---|---|---|---|
| 2010/0089772 | A1* | 4/2010 | Deshusses | G01N 27/127 205/781 |
| 2010/0148780 | A1* | 6/2010 | Lawrence | G01N 27/4045 324/324 |
| 2012/0244358 | A1* | 9/2012 | Lock | C01B 32/194 428/412 |
| 2013/0040283 | A1* | 2/2013 | Star | B82Y 30/00 435/5 |
| 2013/0040397 | A1* | 2/2013 | Star | B82Y 15/00 436/121 |
| 2014/0197046 | A1* | 7/2014 | Busnaina | G01N 27/127 205/786.5 |
| 2014/0231933 | A1* | 8/2014 | Yu | H01L 29/66 257/414 |
| 2014/0260545 | A1* | 9/2014 | Ruhl | G01N 27/124 73/31.05 |
| 2014/0273259 | A1* | 9/2014 | Friedman | G01N 33/0057 436/112 |
| 2015/0086977 | A1* | 3/2015 | Star | G01N 27/4146 435/5 |
| 2017/0321321 | A1* | 11/2017 | Lock | C23C 16/01 |
| 2018/0215623 | A1* | 8/2018 | Lock | G01N 33/50 |
| 2018/0269059 | A1* | 9/2018 | Lin | H01L 29/78696 |

OTHER PUBLICATIONS

Cuong, T. V. et al, Materials Letters 2010, 64, 2479-2482.*
Liu, L.-H. et al, Journal of Materials Chemistry 2011, 21, 3273-3276.*
Zhang, Z. et al, Journal of Materials Chemistry 2011, 21, 17360-17365.*
Lock, E. H. et al, Nano Letters 2012, 12, 102-107.*
Zhang, J. et al, Journal of Materials Chemistry 2012, 22, 714-718.*
Lu, K. et al, Chinese Science Bulletin 2012, 57, 1223-1234.*
Mickelson, W. et al, Applied Physics Letters 2012, 100, paper 173110, 4 pages.*
Zhang, S. et al, Journal of Chromatography A 2012, 1260, 1-8.*
Zhou, L. et al, Nanoscale 2013, 5, 1564-1569.*
Castellanos Aguila, J. E. et al, AIP Advances 2013, 3, paper 032118, 7 pages.*
Nagareddy, V. K. et al, IEEE Sensors Journal 2013, 13, 2810-2817.*
Zhang, J. et al, J. Micromechanics and Microengineering 2013, 23, paper 095031, 8 pages.*
Nagelli, E. et al, Nanotechnology 2013, 24, paper 444010, 7 pages.*
Choi, S.-J. et al, ACS Applied Materials & Interfaces 2014, 6, 2588-2597.*
Abbas, A. N. et al, ACS Nano 2014, 8, 1538-1546.*
Cagliani, A. et al, Nano Research 2014, 7, 743-754.*
Jiang, Z. et al, Journal of Materials Chemistry A 2014, 2, 6714-6717.*
Choi, S.-J. et al, ACS Applied Materials & Interfaces 2014, 6, 9061-9070.*
Zhang, H.-P. et al, Applied Surface Science 2014, 317, 511-516.*
Reshak, A. H. et al, Journal of Applied Physics 2014, 116, paper 103702, 9 pages.*
Lock, E. H. et al, Carbon 2015, 86, 288-300.*
Mohammadi-Manesh, E. et al, Surface Science 2015, 636, 36-41.*
Malek Alaie, M. et al, Journal of Industrial and Engineering Chemistry 2015, 29, 97-103.*
Bai, S. et al, Sensors and Actuators B 2015, 216, 113-120.*
MalekAlaie, M. et al, Materials Science in Semiconductor Processing 2015, 38, 93-100.*
Berahman, M. et al, Sensors and Actuators B 2015, 219, 338-345.*
Huang, Y. et al, Applied Surface Science 2015, 351, 1025-1033.*
Li, Z. et al, Journal of Hazardous Materials 2015, 300, 167-174.*
Chatterjee, S. G. et al, Sensors and Actuators B 2015, 221, 1170-1181.*
Aroutiouian, V. M., Journal of Contemporary Physics (Armenian Academy of Sciences) 2015, 50, 333-354.*

* cited by examiner

GRAPHENE-BASED PPB LEVEL SULFUR DETECTOR IN FUELS

PRIORITY CLAIM

The present application is a non-provisional application claiming the benefit of U.S. Provisional Application No. 62/522,257 filed on Jun. 20, 2017 by Evgeniya H. Lock et al., entitled "GRAPHENE-BASED PPB LEVEL SULFUR DETECTOR IN AVIATION FUELS," the entire contents of which is incorporated herein by reference.

BACKGROUND OF THE INVENTION

Field of the Invention

The present invention relates to detecting ppb levels of sulfur compounds in fuel.

Description of the Prior Art

Fuel cells are of interest to military operations due to their low noise and heat signatures, lower weight, and long life time. A few of the considered military applications include unmanned aerial vehicles (UAV), unmanned ground vehicles (UGV), solders portable power, for silent camp and silent watch operations, as well as for their operation on submarines and ships. On the battlefield JP-8, now FC-24 is the universal logistics fuel, and has a specification that includes up to 3,000 ppm of sulfur but is much more commonly well below 500 ppm. In all fuel cell applications, sulfur must be stripped from the fuel before the fuel is processed or utilized because sulfur is a notorious catalyst poison that rapidly degrades both the anode and cathode electro-catalyst of the fuel cell, as well as the reforming catalysts used in the processing of the higher hydrocarbon fuels to syngas. Whether using JP-8 liquid desulfurizers, or packed bed sorbents for gaseous fuels there is still no inexpensive and reproducible way to identify when sulfur breaks through the desulfurizer. This leaves two possibilities for fuel cell operation: 1) operate the system blindly, assuming that fuel provided was 3000 ppm sulfur laden fuel, thus the system is forced to run very inefficiently, or 2) without knowing whether sulfur has been fully removed the system is forced to assume it is performing as intended, putting at risk a very expensive fuel cell asset. It should be noted that solid oxide and PEM fuel cells, cannot operate with sulfur concentrations of even 3 ppm without seeing significant loss of active catalyst material and rapid degradation in performance.

Graphene is an excellent sensor material as it is composed entirely of surface atoms, with exceptional physicochemical properties including high specific surface area, high carrier mobilities, and extremely low noise characteristics. Being all surface, the electronic properties of graphene show a strong dependence with surface adsorbates that can alter the charge carrier concentration of graphene leading to measurable changes in conductivity. The mechanism is likely due to charge transfer from or to the adsorbed molecule; the resulting change in the sheet charge density of graphene leads to a change in conductance which can then be subsequently measured. Pristine, mechanically exfoliated graphene can be highly sensitive to a variety of gas species such as $NH_3$, CO, $NO_2$, $H_2$, and $CO_2$, at parts-per-billion and higher concentrations. Even though graphene is extremely sensitive, it is not selective because of the lack of dangling bonds in the graphene structure. Thus, the use of pristine graphene fails when other interfering agents and conditions occur e.g. humidity, presence of other gas and organic molecules etc. The solution is to functionalize graphene to increase its selectivity. In fact, selective chemical functionalization of epitaxial graphene with oxygen moieties can increase the sensitivity of a room temperature conductometric device towards organic vapors such as methanol, chloroform, acetonitrile, toluene, tetrahydrofuran, with fast response (10 sec) and recovery times (~150 sec) and good repeatability (Nagareddy et al., "Improved Chemical Detection and Ultra-Fast Recovery Using Oxygen Functionalized Epitaxial Graphene Sensors," IEEE Sensors Journal, 13, 8 (2013)).

Metal oxides have been of technological interest in sensing applications for nearly two decades due to the enhanced sensitivity from trapped surface states and carrier depletion within nanocrystallites. The high degree of crystallinity achieved in some metal oxide nanostructures can also provide greater long term high temperature stability desired for commercial devices. It has been demonstrated that the sensing performance and selectivity towards sulfide containing analytes can be significantly enhanced when nanomaterials (such as carbon nanotubes) are functionalized with appropriate oxide materials.

BRIEF SUMMARY OF THE INVENTION

The present invention provides graphene decorated with metal oxides, such as CuO, ITO, $Fe_2O_3$, ZnO, as the transducing and sensory elements of a chemiresistor sensor for the in-line detection of ppm levels of sulfur contaminates in fuels. A graphene based ppb level sulfur detector was created using UV-activated chemical functionalization and attachment of metal oxide nanoparticles to graphene through a chemical linking molecule. The metal oxide nanoparticle types may include ZnO, CuO, indium-tin oxide (ITO) and $F_2O_3$. Bare and functionalized graphene devices were exposed to pure synthetic fuel S8 containing no sulfur, JP8 aviation fuels with 20 ppm and 600 ppm sulfur and mixtures of S8 with the most common sulfur compounds found in aviation fuels—octanethiol (mercaptans), thiophene and benzothiophene. Fuels in both liquid and gas phases were tested.

Potential applications for graphene/metal oxide hybrid sensors include but are not limited to fuel cell power generation assets, portable fuel sensors for identifying "good" and "bad" fuel quickly for use in sulfur-sensitive applications, portable tools for the oil and gas industry, fuel cell lab test equipment, and use in automotive fuel cell vehicles.

Some advantages of the present invention include fast sensor response time 30 seconds for the gas-phase sensors and 3 minutes for liquid sensing); device selectivity towards thiophene, octanethiol and benzenthiophene in synthetic S8 fuel mixtures; device reactivity towards JP8 aviation fuel containing 20 and 600 ppm of sulfur in both gas and liquid phases; faster kinetics at elevated temperatures (response time of 10 seconds); device recovery using external heating to 125° C. prior testing at room temperature or using isopropanol rinse; and device sensitivity of 4 ppb for benzothiophene, 6 ppb of octanethiol and 5 ppm range for thiophene with predicted limits of detection in low ppt regime (<4 ppb).

Thus, a combination of pure graphene and graphene/metal oxide hybrid detectors on one chip (a system of detectors) will pave the way to a new class of sulfur sensing technology. Note that the current technology analyzes the fuel after it has been burned (SO, $SO_2$ species). In this invention, we present a method for detection of sulfur compounds in fuel that is still intact.

These and other features and advantages of the invention, as well as the invention itself, will become better understood by reference to the following detailed description, appended claims, and accompanying drawings.

BRIEF DESCRIPTION OF THE DRAWINGS

FIG. 16A is for device 1. FIG. 16B is for device 2. FIG. 16C is for device 3. FIG. 16D is for device 4.

DETAILED DESCRIPTION OF THE INVENTION

Figure 1:
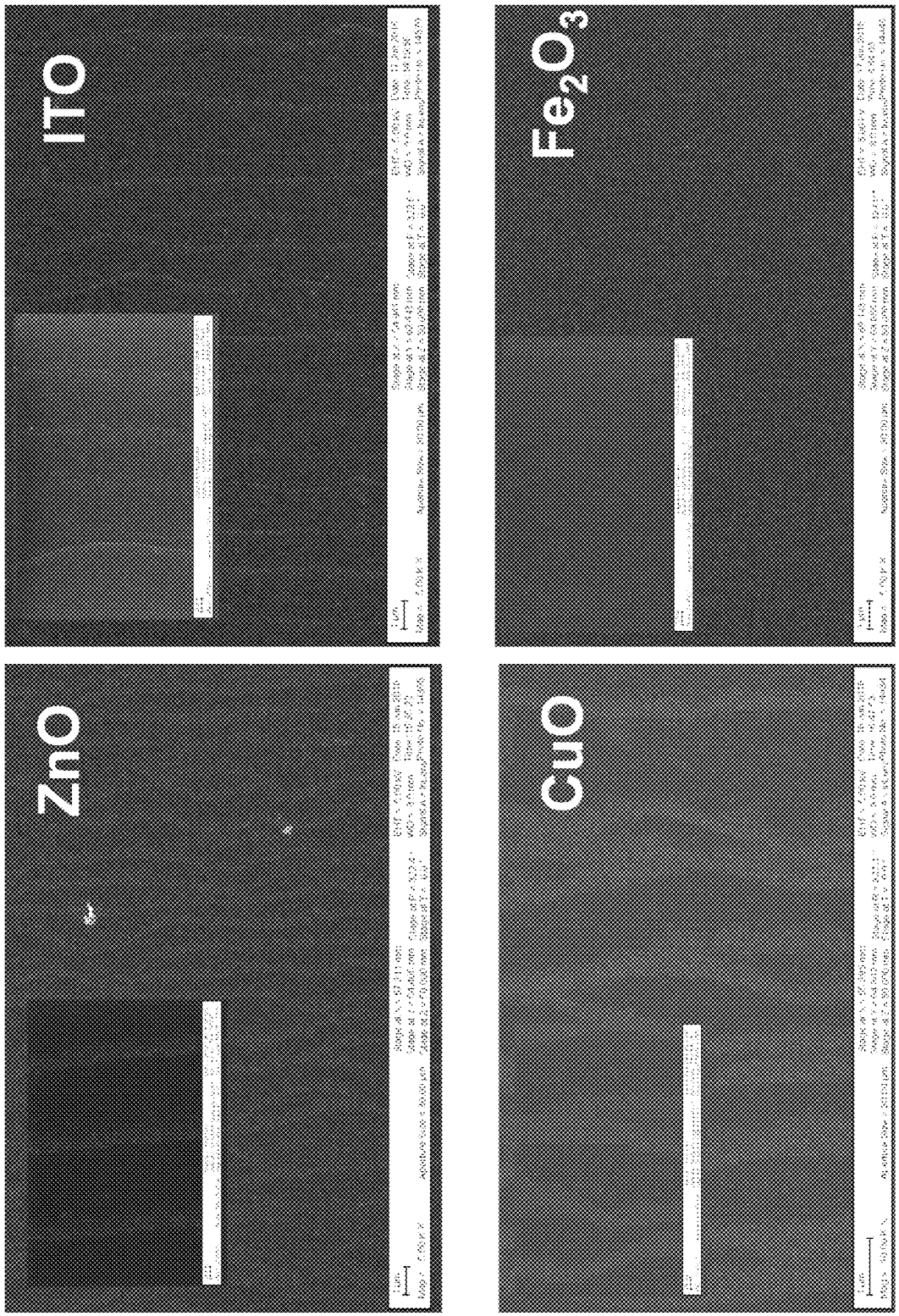
FIG. 1 shows SEM images of graphene films functionalized with ZnO, ITO, CuO, and $Fe_2O_3$ nanoparticles.

The present invention addresses the need of knowing the sulfur concentration in fuel by utilizing hybrid graphene/metal oxide nanoparticle material systems. Chemiresistive sensor technologies based upon two-dimensional (2D) materials (graphene, $MoS_2$, etc.) require low power, have high signal/noise ratios, enable fast detection and allow for detection of molecules that have not been detected before. Graphene is an excellent sensor material. Since sensors made from 2D materials are responsive to a vast range of molecules, it is necessary to tune the selectivity to the target molecule. In this regard, metal oxide nanoparticles (NP) are attractive since nanostructured metal oxides and NP array sensor implementations have outperformed 3D (bulk) counterparts. This has been attributed to large surface-to-volume ratios, dimensions comparable to the surface charge region, and a high degree of crystallinity that yields superior stability. The sensing performance and selectivity towards sulfide containing analytes can be significantly enhanced when nanomaterials (such as carbon nanotubes) are functionalized with appropriate oxide materials and detectivity reaching sub parts per billion (ppb) level detection have been attained. In addition, different metal oxides are known to be more or less sensitive to sulfur-containing molecules. Four different nanoparticle metal oxide nanoparticle types are of interest: indium tin oxide, zinc oxide, copper oxide and iron oxide.

Finally, it should be noted that sensor gas selectivity, sensitivity, response time and recovery are dependent upon the 2D material composition as well as device geometry, and typically the behavior of these 2D-nanoparticle hybrid systems are different from the individual components due to changes in electronic structure and sensing mechanism.

Hybrid Material Production

Graphene was chemically functionalized using one step UV-enabled approach during which nanoparticles dispersed in $TFPA-NH_2$ linker solution in methanol. This approach was applied various metal oxide nanoparticles (ZnO, CuO, ITO and $F_2O_3$) and can be expanded to any type of oxide nanoparticle. Then, devices were fabricated and tested with pure synthetic fuel, synthetic fuel mixtures with sulfur containing compounds and JP8 fuels containing different sulfur concentrations. In both cases graphene was synthesized by means of Si sublimation from semi-insulating (SI), Si-face, on-axis, 6H-silicon carbide (SiC) substrates. The growth took place in a chemical vapor deposition reactor at a temperatures between 1540 and 1580° C. and a pressure of 100 mbar using Ar ambient. The Ar was used to suppress the sublimation of Si in order to control the thickness of the epitaxial graphene layers. Prior to growth, the substrates were in-situ $H_2$ etched to prepare the SiC surface for epitaxial graphene growth, by forming bilayer stepped morphology and removing any polishing scratches created during the manufacturing of the SiC substrate. Samples were cooled in Ar to 800° C., at which point the reaction tube was evacuated. The average thickness of the epitaxial graphene was ~1.5 monolayers as measured by X-ray photoelectron spectroscopy (XPS, spot size 400 µm). It should be noted that although graphene grown epitaxially on SiC was used for the functionalization experiments described below, the functionalization strategies can be applied to chemical vapor deposited (CVD) and exfoliated graphene as well.

Attaching Nanoparticles to Functionalized Graphene

Nanoparticle Attachment

Four different types of metal oxide nanoparticles were attached to graphene using TFPA-$NH_2$ as a chemical linker. The nanoparticles used include zinc oxide nanopowder dispersion (ZnO, 20 wt %, 50-80 nm), copper oxide nanopowder water dispersion (CuO, 99.95+%, 25-55 nm, 20% in water), iron oxide nanopowder water dispersion ($Fe_2O_3$, alpha phase, 20%, 20-100 nm), and indium tin oxide (ITO) nanopowder water dispersion ($In_2O_3$:$SnO_2$=9:1, 18 nm, 20 wt %, blue color) purchased from US Research Nanomaterials Inc. The attachment protocol was as follows. First, a series of base nanoparticle dispersions were produced (Table 1). Then, the base dispersions were further diluted in methanol to avoid agglomeration. Some nanoparticle dispersions were sonicated for approximately 15 minutes to enable better dispersion. Then, TFPA-$NH_2$ solutions in methanol were added and nanoparticles were incubated for 1 hour at room temperature. After that epitaxial graphene/SiC chips were placed in the solutions and the dispersion was exposed to a 460 W Hg UV lamp (Oriel instruments) for 20 minutes. The samples were then rinsed with methanol and isopropanol. The nanoparticle attachment was verified by scanning electron microscopy (SEM) (see FIG. 1). This functionalization scheme can be extended to any oxide nanoparticle and by changing the amine functionality with thiol sulfide-based (e.g. CdS) quantum dots can be attached as well.

TABLE 1

Base nanoparticle dispersion

| NP type | NP size (nm) | NP dispersion volume (µl) | MeOH volume (ml) |
|---|---|---|---|
| ZnO | 50-80 | 25 | 20 |
| CuO | 2-55 | 10 | 100 |
| $Fe_2O_3$ | 20-100 | 10 | 100 |
| ITO | 18 | 25 | 20 |

Device Fabrication

There was no a priori knowledge which device geometry would be best suited for chemiresistive sensing experiments. In fact, based on the literature results, most of the chemical sensors have interdigitated geometry or they have open area with unpatterned graphene. However, we realized that most of the chemical functionalization happens at defect sites and we engineered defects by graphene patterning and compared them to the sensor performance with unpatterned graphene. In both cases, Ti/Au contacts were evaporated. For the latter, a modified bi-layer recipe was employed to obtain 1) low graphene-metal contact resistance and 2) a clean post-fabrication graphene active region (see Nath et al. "Achieving clean epitaxial graphene surfaces suitable for device fabrications by improved lithographic process," APL 104, 22, 224102 (2014) and Nath et al., "In search of quantum-limited contact resistance: Understanding the intrinsic and extrinsic effects on the graphene-metal interface," 2D Materials 110 (1), 013106 (2016)).

Figure 2:
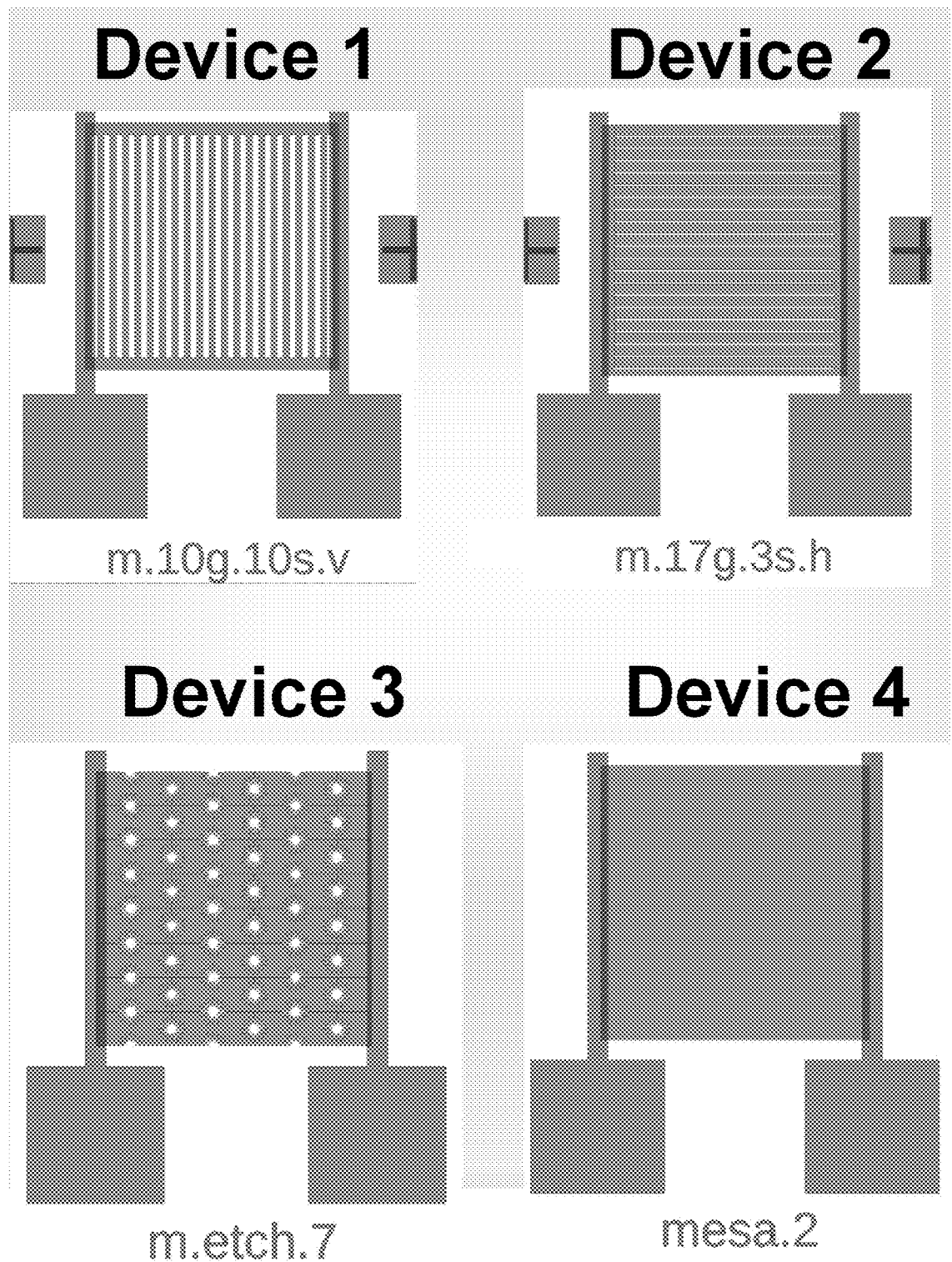
FIG. 2 shows device geometries being tested. Device 1 has a mesa structure in which graphene was etched into 10 µm line/space pairs configured perpendicular to the applied field. Device 2 has a mesa structure in which graphene was etched into 17 µm wide strips and 3 µm wide spaces parallel to the applied field. Device 3 has an etched star area. Device 4 is unpatterned graphene.
Figure 3:
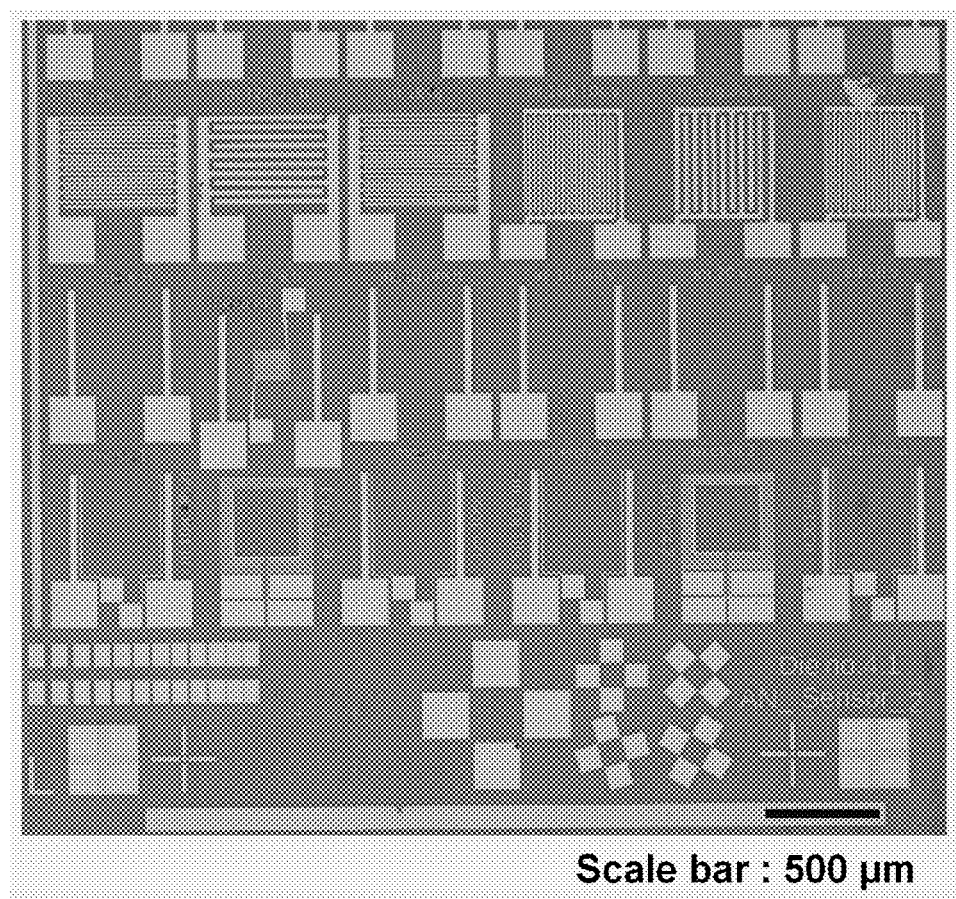
FIG. 3 is an optical image of a sample fabricated chip used in testing. In this image, the graphene pattern is not visible.

After electrical evaluation was completed, four device structures as shown in FIG. 2 were identified for exposure to chemical testing. Device 1 (D1) had a mesa structure in which graphene was etched into 10 µm wide strips and 10 µm wide spaces perpendicular to the applied field (and thus perpendicular to the direction of charge transport). Device 2 (D2) had a mesa structure in which graphene was etched into 17 µm wide strips and 3 µm wide spaces, parallel to the applied field. While device 3 (D3) had an etched area with a dense array of multidentate star features, device 4 (D4) had an unpatterned graphene surface. Although not disclosed herein, other etching patterns may be used. FIG. 3 shows an optical image of a fabricated chip.

Figure 4:
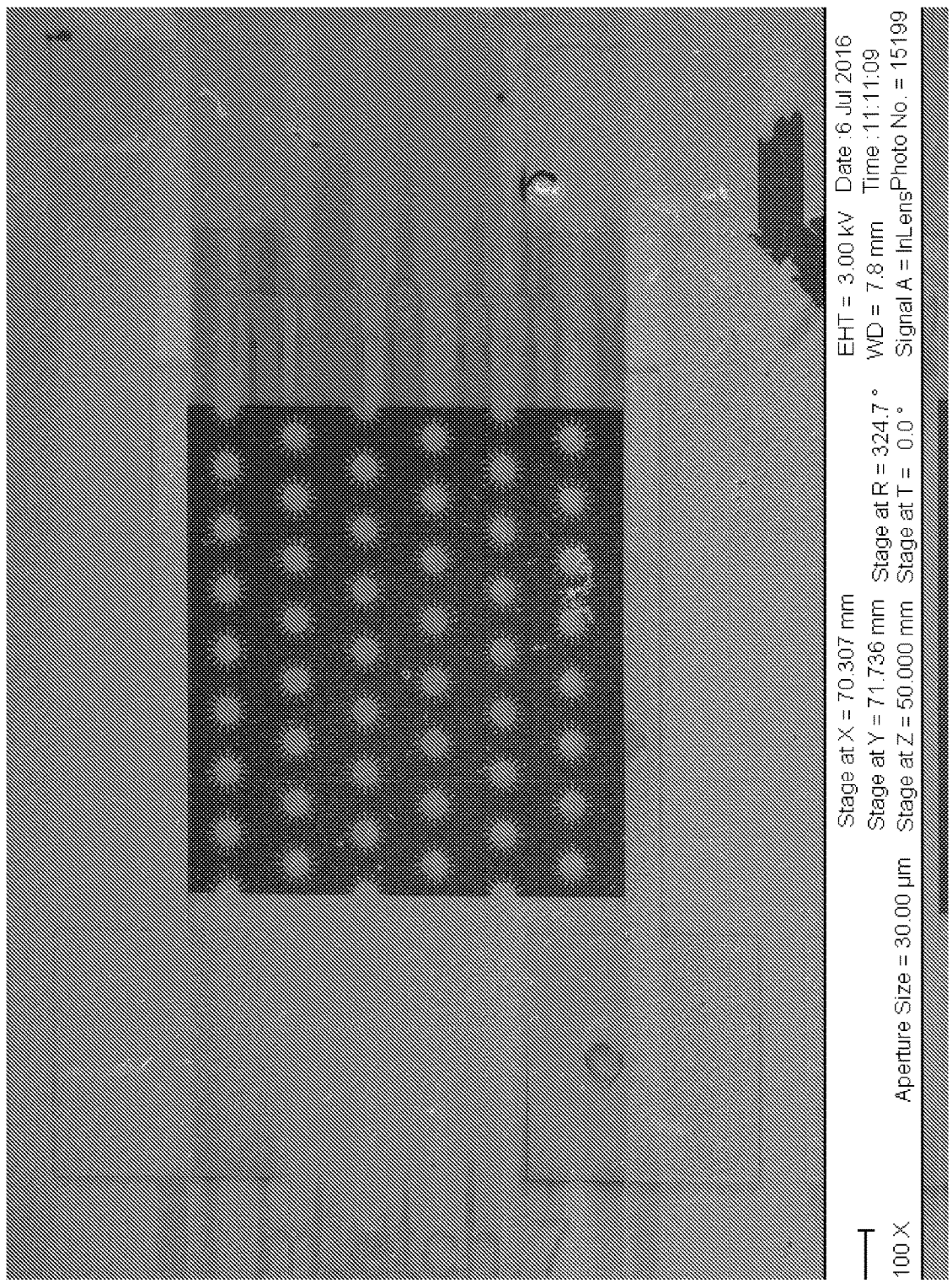
FIG. 4 is an SEM image of a functionalized device.
Figure 5:
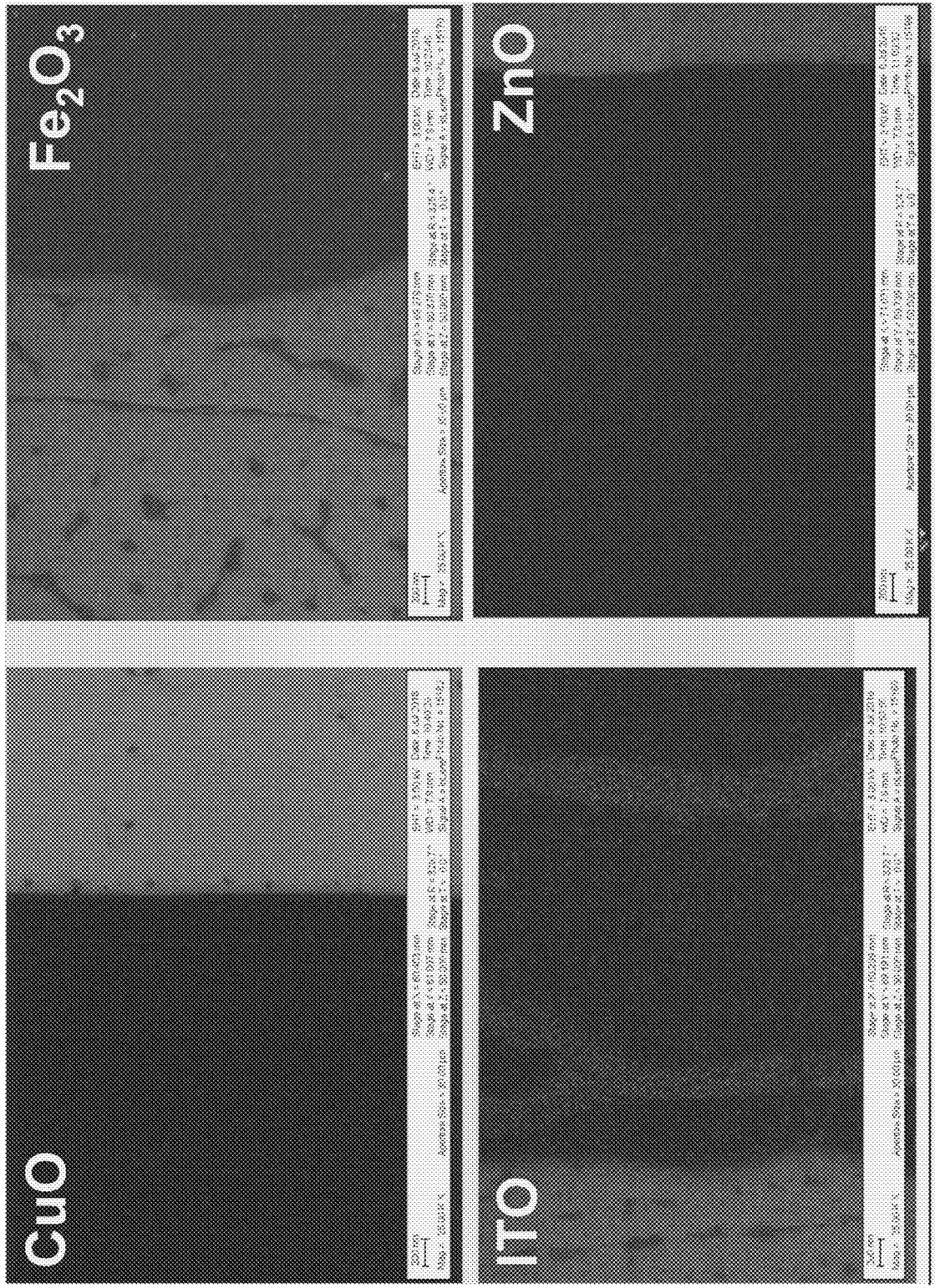
FIG. 5 shows high resolution SEM images of graphene surface of functionalized devices.

Using the most effective nanoparticle dispersion conditions, graphene films and fabricated devices were functionalized with ZnO, CuO, $Fe_2O_3$ and ITO nanoparticles. An example of a functionalized graphene device (D3) is shown in FIG. 4, and higher magnification images of D3 with each functionalization are shown in FIG. 5. It is clear that the functionalization was successful and coverage depends on the nanoparticle type.

Device Testing

Following fabrication, the devices were tested with pure synthetic fuel, synthetic fuel mixtures with sulfur containing compounds, and JP8 fuels containing different sulfur concentrations in liquid and gas phase.

Testing Facilities

Figure 6:
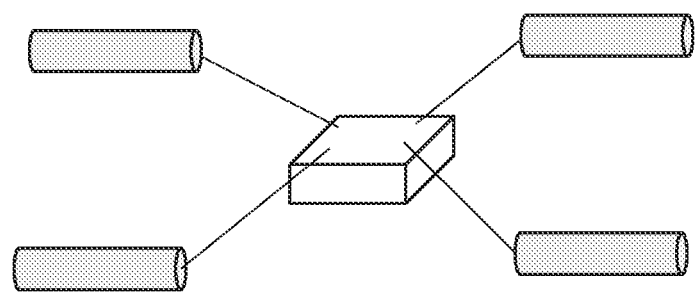
FIG. 6 shows a Hall effect measurement system used for liquid fuel testing.
Figure 7:
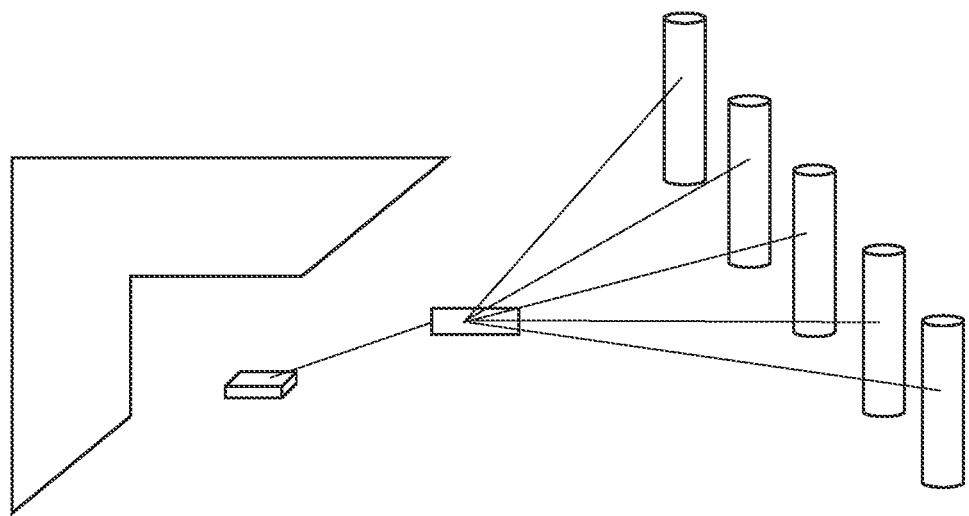
FIG. 7 shows a gas phase sensor testing system. To the right are five parallel bubblers for generating dilute vapors, to the left is the probe station with inspection binocular microscope. The apparatus is enclosed within a well-ventilated hood.

Different testing facilities were employed to quantify sensor chemiresistive response to fuel mixtures in liquid phase and in gas phase. A Hall measurement system shown in FIG. 6 was used for the liquid fuel testing. The chip was positioned at the center, so that the probes could reach the pattered gold contacts. Liquid fuel was drop casted onto the chip and the electrical properties were measured over a period of 30 minutes. A more sophisticated system was utilized for the gas phase testing as shown in FIG. 7. Devices were each contacted with a pair of Au-coated W probes on a conventional probe station (see FIG. 7) attached to computer-controlled lock-in amplifiers. The probes were connected to either a low-impedance voltage source $V_s$=0 $V_{dc}$+0.1 $V_{ac,rms}$ with frequency on the order of 2 kHz, a different frequency for each device, or a device-impedance matched (0.1-10 kΩ) bias resistor $R_b$ in parallel with the 10 MΩ input impedance of the lock-in amplifier, so that the lock-in amplifier measures the voltage drop across the resistor at the reference frequency. In this way, we measured small voltage changes ΔV across $R_b$ corresponding to small changes in differential conductance $(G-G_0)/G_0$ of multiple devices on a single substrate with high signal-to-noise ratios. Substrates were placed on a sample chuck with heating capabilities for elevated temperature operation, with the temperature being monitored by a thermocouple contacting the top face of the substrate. Devices were constantly under ac source-drain bias while intermittently exposed to vapors of various fuel-sulfur mixtures (see below). Vapors were generated by first bubbling low flows, 0-100 sccm pure, dry $N_2$, through a glass frit immersed in about 15-25 ml of analyte. The outflow from this, generally presumed to be saturated with vapor from the liquid, was mixed with a constant 200 sccm flow of $N_2$ in order to reduce the likelihood of liquid condensing in the solenoid valve directing vapor to the device under test (DUT) or the system exhaust. When directed to the DUT, it was mixed with another constant flow of 4.8 lpm to achieve a range of dilution between 0.02 and 2%.

Liquid Phase Fuel Testing

Figure 8:
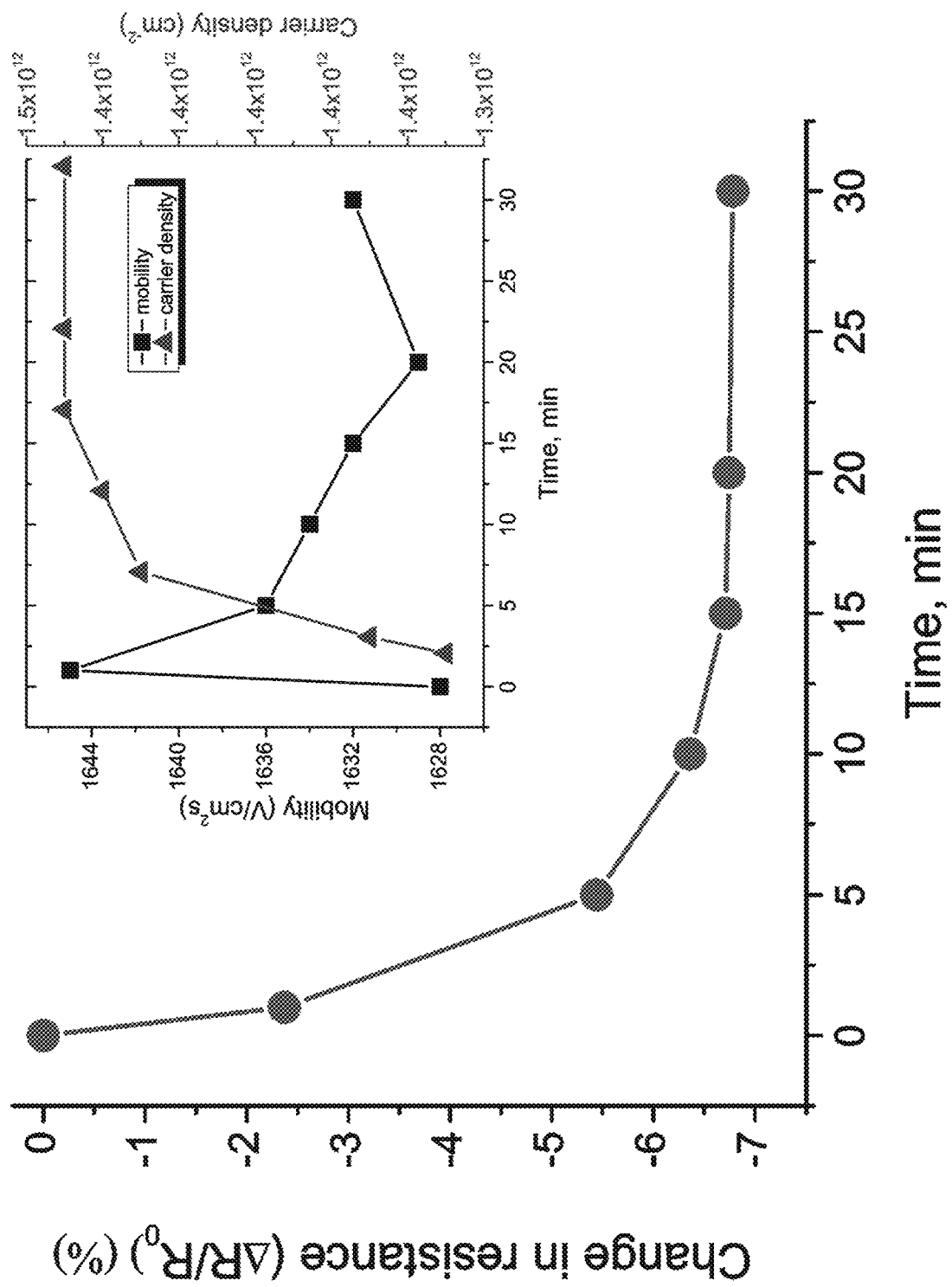
FIG. 8 shows the resistance change of a $TFPA-NH_2$ chemically functionalized graphene device which had metal pads on four corners. The resistance was measured in Hall effect geometry after immersion in JP8 fuel containing 400 ppm of sulfur.
Figures 9A, 9B:
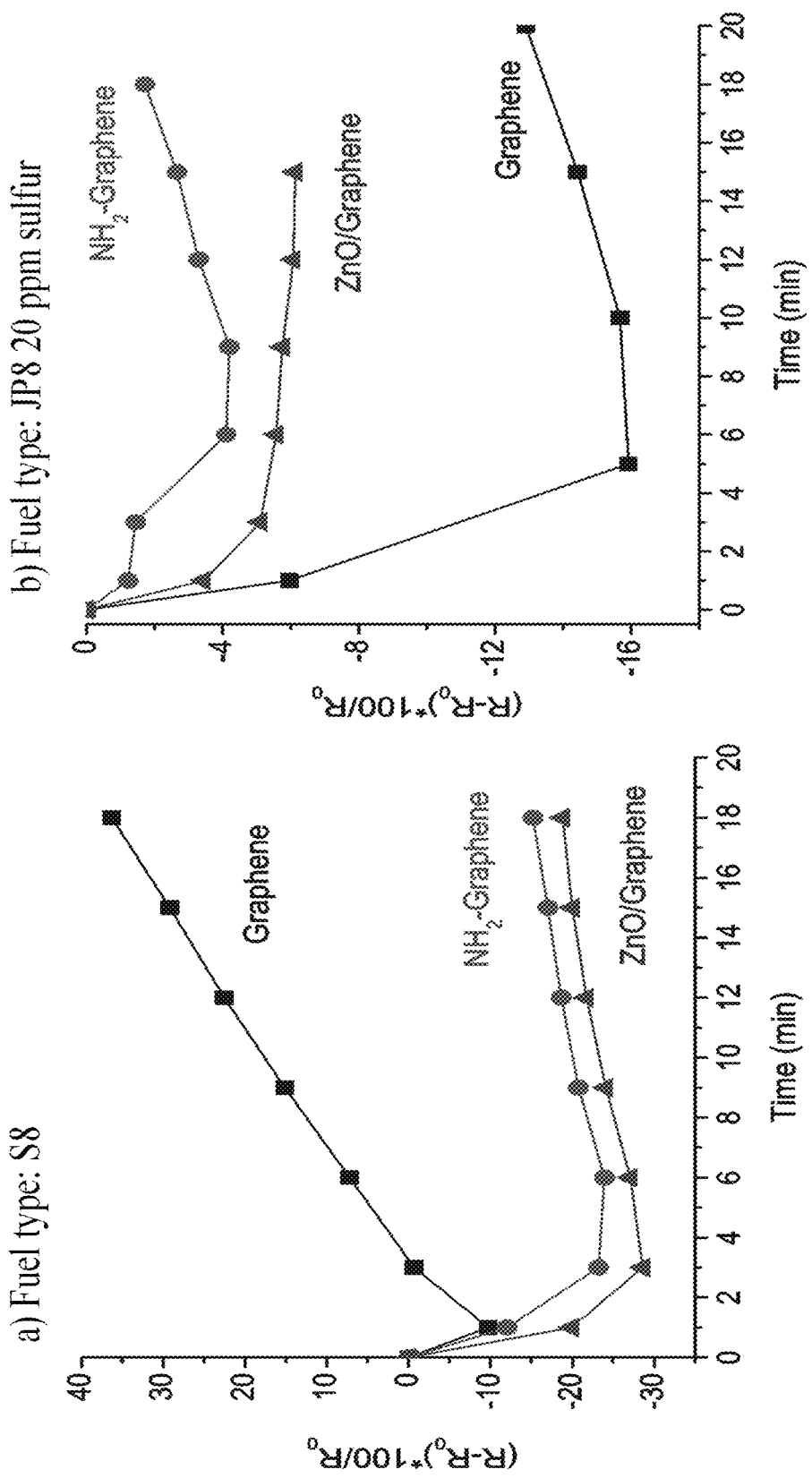
FIG. 9A shows the resistance change after liquid fuel immersion testing of bare graphene, chemically functionalized $TFPA-NH_2$, and ZnO-Gr using synthetic fuel with 0 sulfur content (S8).
FIG. 9B shows the resistance change after liquid fuel immersion testing of bare graphene, chemically functionalized $TFPA-NH_2$, and ZnO-Gr using aviation fuel JP8 with 20 ppm sulfur content.
Figure 10A:
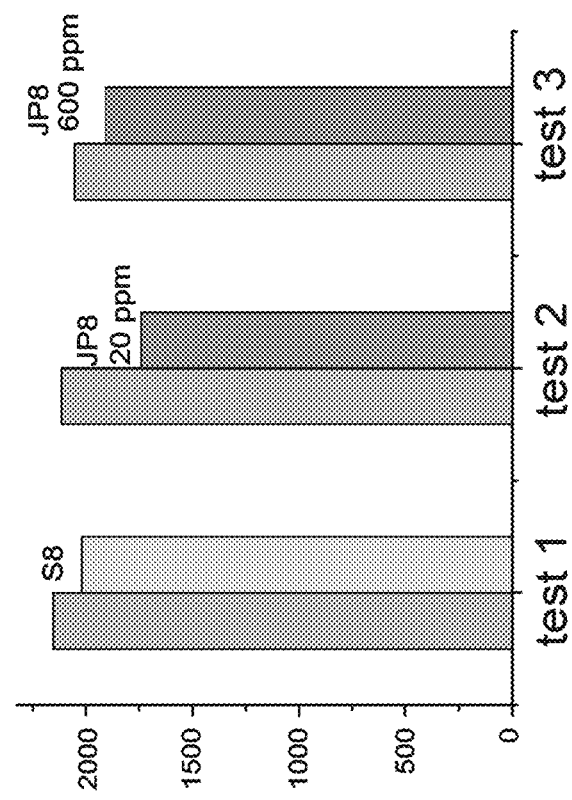
FIG. 10A shows a $TFPA-NH_2$ functionalized graphene sensor recovery after isopropanol rinse.
Figure 10B:
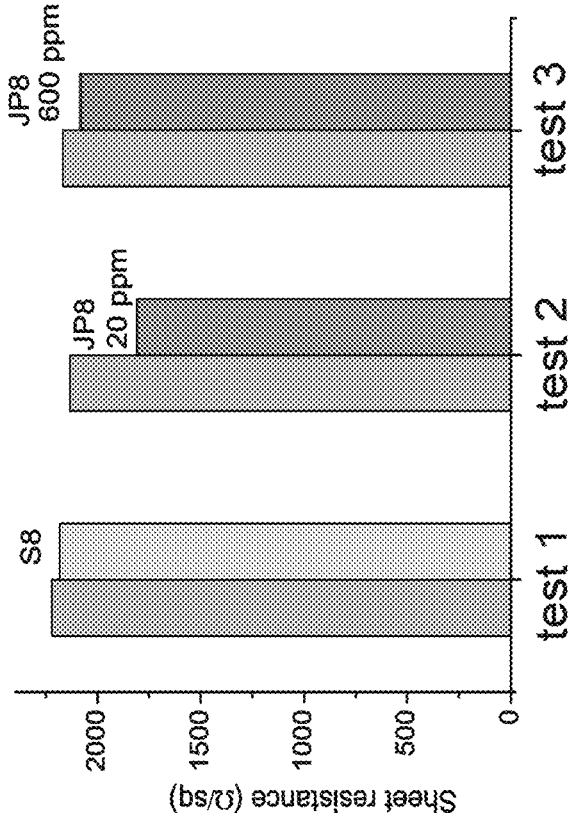
FIG. 10B shows a ZnO/Graphene sensor recovery after isopropanol rinse.

A Hall bar patterned device was wirebonded and tested in the Hall effect measurement system before and after drop casting of 400 ppm sulfur containing JP8 aviation fuel. The results from the tests are shown in FIG. 8. The device had a relatively fast negative response with resistance change of 7% within 10 minutes. It should be noted that the mobility and carrier density of graphene tracks the resistance change. To extend and simplify the measurement above, the following approach was used. Graphene on SiC chips were laser ablated to isolate four squares and then Ti/Al was deposited at the corners through a shadow mask. Then, synthetic fuel S8 with zero sulfur content as well as JP8 fuels with 20 ppm and 600 ppm unidentified sulfur content were drop cast onto the chips and the change in resistance was measured. The chips tested were bare graphene, TFPA-$NH_2$ and ZnO nanoparticle functionalized. The response of the films over 20 minutes of testing with JP8 20 ppm sulfur and S8 are shown in FIG. 9. With synthetic fuel, the bare graphene chip has a positive response, while the functionalized chips have a negative response. With JP8 fuel, all tested chips had a negative response. The sensor recovery was achieved by rinsing the chips with isopropanol, as shown in FIG. 10 where the measured sheet resistance before and after isopropanol rinse are compared. The observed trend was valid for all tested chips.

Graphene, TFPA-$NH_2$ molecule and ZnO nanoparticle functionalized devices responded to synthetic and JP8 fuels. Detectable differences in response signature (positive for S8+graphene, negative for S8, JP8+functionalized devices) were measured. The response magnitude was a function of device functionalization type in the case of JP8 testing. Simple isopropanol rinse of the chips was sufficient for device recovery at room temperature.

Gas Phase Fuel Testing

Sensor Sensitivity Testing

Bare graphene and ZnO, ITO, $Fe_2O_3$ and CuO nanoparticle functionalized graphene devices at room and elevated (125° C.) temperatures were exposed to pure S8, S8 and sulfur compound mixtures (S8+1000 ppm w/w n-octanethiol (S8+8T), S8+1000 ppm w/w of thiophene (S8+Th), S8+1000 ppm w/w of benzothiophene (S8+BzT)), and JP8 with 20 ppm and 600 ppm unidentified sulfur content. It is important to realize that the composition of the vapor head space is not a simple function of the nominal composition of the liquid. To first order, the vapor composition at pressure P can be given by $\Sigma_i x_i P_{0,i}$, where $x_i$ is the mole fraction of each component i in the mixture ($\Sigma_i x_i = 1$) and $P_{0,i}$ is the temperature-dependent equilibrium vapor pressure of each component. Deviations from this simple relationship (known as Raoult's law) can occur in either direction, depending on the nature and strength of the interaction between the various molecules, and can be especially significant for dilute species. Furthermore, it is obvious that as the more volatile constituents evaporate from the liquid, the composition of the liquid changes, and that is reflected in the composition of the vapor. For this reason sensor data acquisition is accompanied by analyte and substrate temperature monitoring as well as vapor characterization with a residual gas analyzer (RGA) configured with differential pumping to allow sampling at atmospheric pressure. By measuring the RGA response at characteristic masses observed in known dilutions of vapor from pure compounds at a known temperature we are able to determine the relationship between RGA counts and vapor partial pressure. We can then use this information to determine the partial pressure of particular compounds in the dilute vapor head space over a mixture.

In this way, we established a typical concentration of thiophene in the vapor over 1000 ppm w/w in S8 at room temperature diluted to 2% of equilibrium of 8 ppm, and of benzothiophene similarly diluted, 260 ppb. Even though not experimentally verified based on Raoults' law prediction, the concentration of octanethiol in S8 that the sensors were exposed to was in the 50 ppb range as well. Given the high concentration of sulfur compounds in S8 of a 1000 ppm and the high sensor response as shown below, the detection limits of these sensors is in the low ppb range (<30 ppb). In follow-up testing, we verified that the sensitivity of the functionalized graphene devices towards S8+benzothiophene mixture is better than 4 ppb. In this experiment the fabricated devices were one year after fabrication.

Sensor Selectivity Testing

The procedure for device testing was as follows. A chip was heated on a hot plate in air at 125° C. for 5 minutes to ensure sensor recovery. Then, the chip was placed quickly under flowing $N_2$, and the four devices were contacted by the eight probes and for at least 30 minutes allowed to equilibrate back to room temperature (25-30° C.). High temperature experiments (125° C.) required heating the $N_2$ stream to avoid cooling the sample, and careful adjustment of probe contacts as the chip equilibrated to the elevated temperature of the chuck. The exhaust stream was monitored by the RGA to confirm sulfur compound level. The analyte was replaced as needed with fresh fuel/sulfur compound mixtures. It should be noted that the experiment setup for the results presented below was to have nitrogen bubble through S8/sulfur compounds mixture solutions. In the later day we have separate bubblers for S8 and for the three sulfur compounds that allowed better control over dilution ratios. However, in both experimental setups the graphene devices exhibited high sensitivity and selectivity. The data collection process had the following steps: a) 300 s to establish baseline; b) a pulse sequence, typically 5 pulses 33 s on, 99 s off; c) LIAs (lock-in amplifiers), substrate temperature, and bubbler temperature sampled synchronously at ~1 Hz; d) gas composition monitored asynchronously in parallel. On a given chip with common functionalization, four devices (D1-D4) were evaluated simultaneously. Table 2 lists the 20 possible devices with (if evaluated) the response direction or absence depicted as follows: "N" for no response; "+" for positive response and "−" for negative response. Devices with line space pairs (D1, D2) gave the most consistent and reliable response, while the internal edge shaped geometry (D3) and unpatterned graphene (D4) had weak or no response. So, the data only devices D1 and D2 were further analyzed with the results shown below. The D1 and D2 of the ITO functionalized graphene device were found to be the most consistent and gave the best results.

Figure 11:
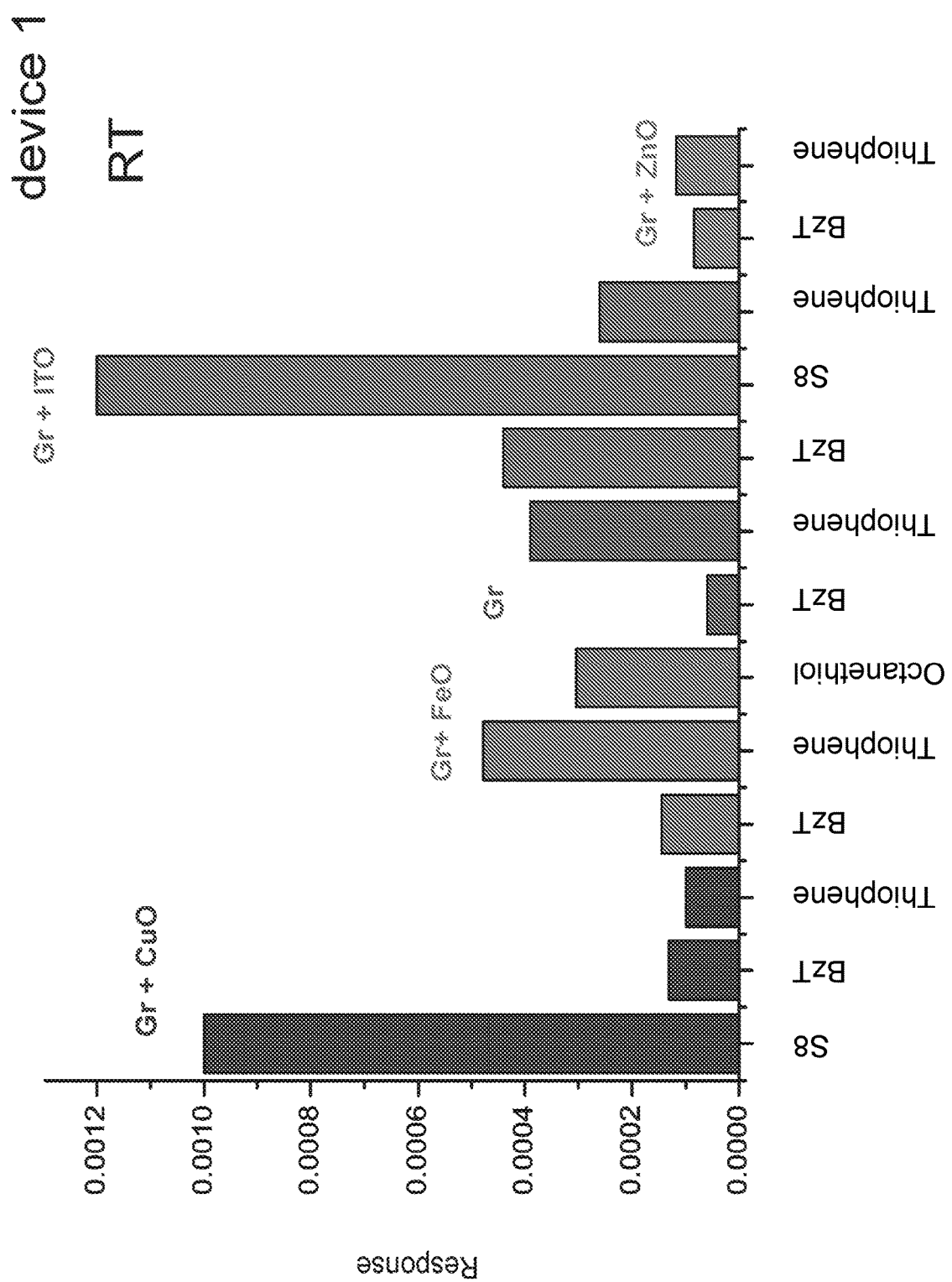
FIG. 11 shows a plot of detector response at room temperature exposure for device 1 on bare and CuO, FeO, ITO, and ZnO functionalized devices to pure synthetic fuel S8 with zero sulfur content and mixtures of S8 with 1000 ppm of the following three sulfur containing compounds: thiophene, benzothiophene, and octanethiol. The response is measured relative conductance $(G-G_0)/G_0$.
Figure 12:
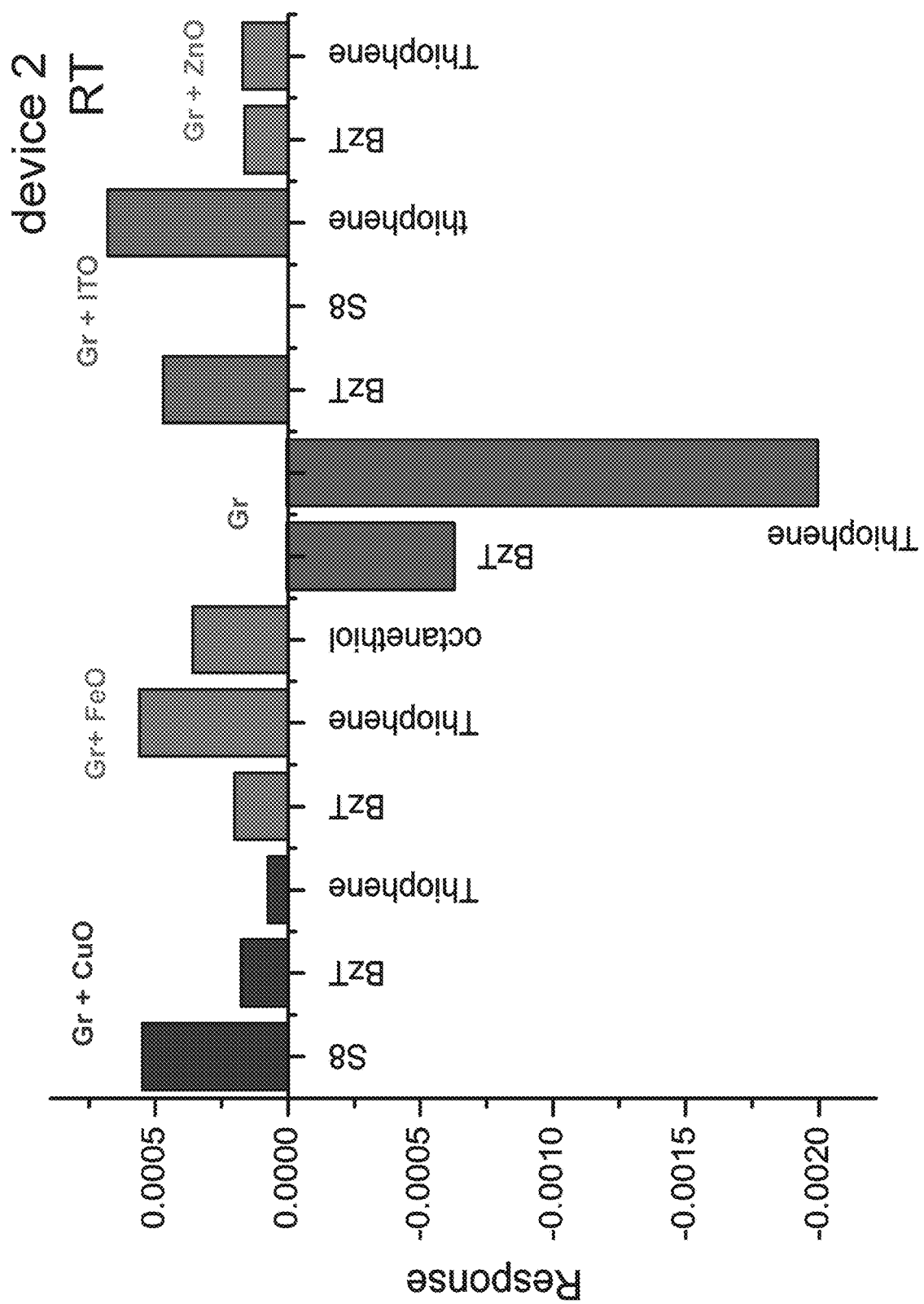
FIG. 12 shows a plot of detector response at room temperature exposure for device 2 on bare and CuO, $Fe_2O_3$, ITO and ZnO functionalized devices to pure synthetic fuel S8 with zero sulfur content and mixtures of S8 with 1000 ppm of the following three sulfur containing compounds: thiophene, benzothiophene, and octanethiol. The response is measured relative conductance $(G-G_0)/G_0$.

The observed trends of the performance of devices D1 and D2 at room temperature are summarized in FIGS. 11 and 12 respectively. As shown in FIG. 11, the bare graphene and the four different functionalization types had remarkable selectivity to S8+sulfur compounds mixtures. For example, the response to S8+Thiophene of all five sensors was completely different. Note that "S8+8T", "S8+Th", "S8+bzT" in Table 2 denotes mixtures of S8 and octanethiol, thiophene and benzothiophene. There were also differences in the magnitude of the response—the highest response to S8 was from ITO-Gr, followed by CuO-Gr sensors. While the latter sensors showed very small differentiation between sulfur containing compounds, the differences in the responses of the ITO-Gr devices was significant. Similar to ITO-Gr, the $Fe_2O_3$-Gr devices showed good differentiation between sulfur-containing compounds with similar signal strengths. The ZnO-Gr device showed limited differentiation between S8+BzT and S8+th mixtures. Changing the device geometry (FIG. 12) did introduce some response changes, most noticeably in the case of the bare graphene devices, when there was a sign reversal and increase in response to S8+BzT and especially to S8+Th by almost an order of magnitude. CuO-Gr device was less sensitive to S8—almost a factor of two reduction in response, while the response to S8+sulfur containing mixtures did not change. Both ITO-Gr and $Fe_2O_3$-Gr devices showed good selectivity, while the ZnO-Gr device had none.

increased in response to JP8 600 ppm. It should be also noted that the response of device 1 exposed to JP8 20 ppm and 600 ppm did not increase 30 fold, proportional to the sulfur content.

Sensor Selectivity as a Function of Testing Conditions—Temperature Effect

Figure 15:
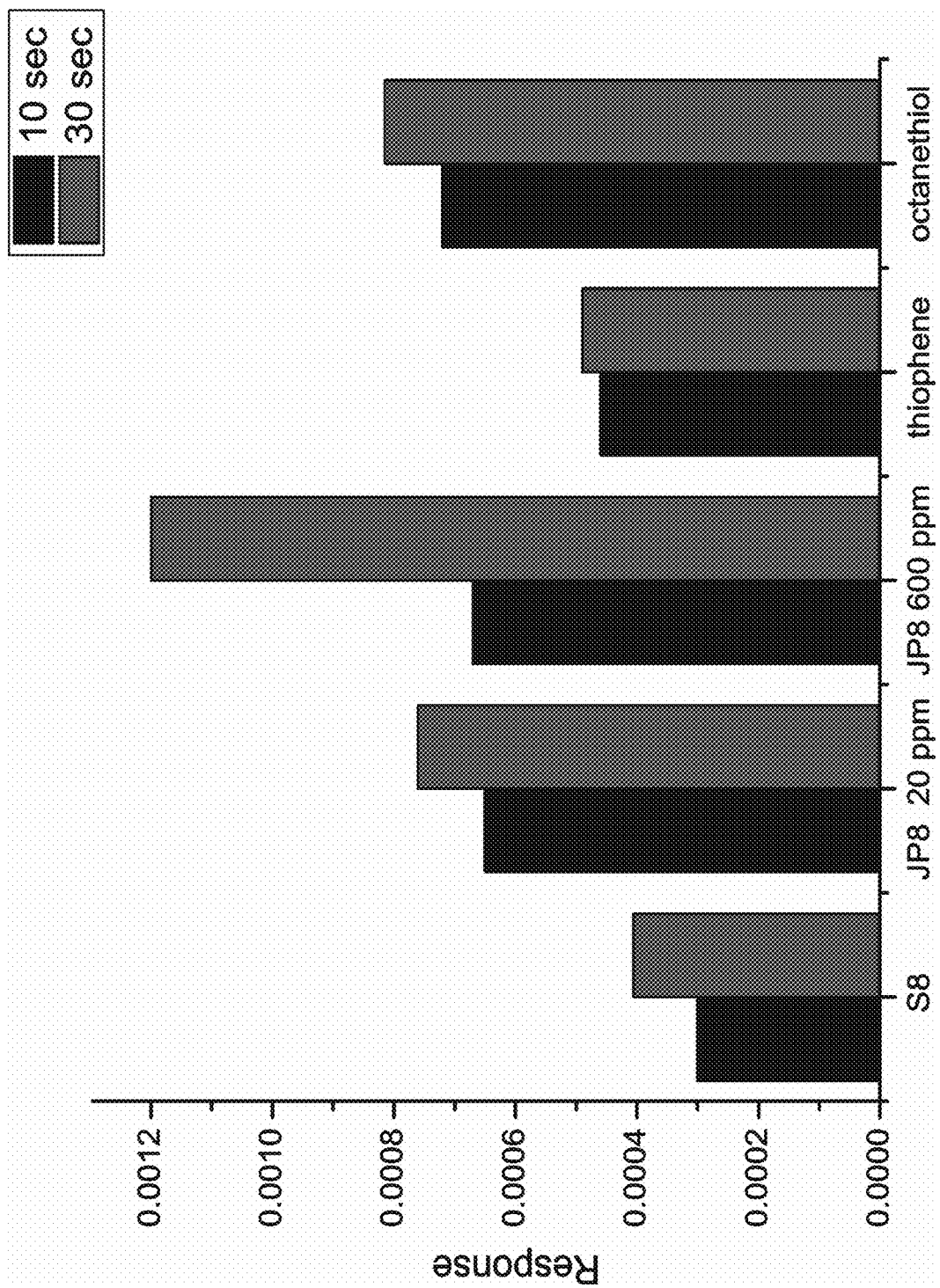
FIG. 15 shows a plot of ITO functionalized device response exposed to synthetic fuel (S8), aviation fuels JP8 containing 20 ppm and 600 ppm of sulfur, and S8+thiophene, and S8+octanethiol mixtures. The response was measured after 10 and 30 seconds of exposure at 125° C. The response is measured relative conductance change, $(G-G_0)/G_0$.
Figure 16A:
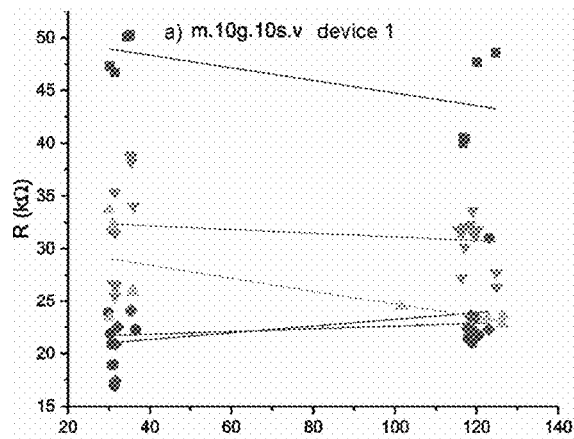
FIGS. 16A-16D shows device consistency with resistance measurements prior to each experiment for all five functionalized devices for the room temperature and elevated temperature experiments.
Figure 16B:
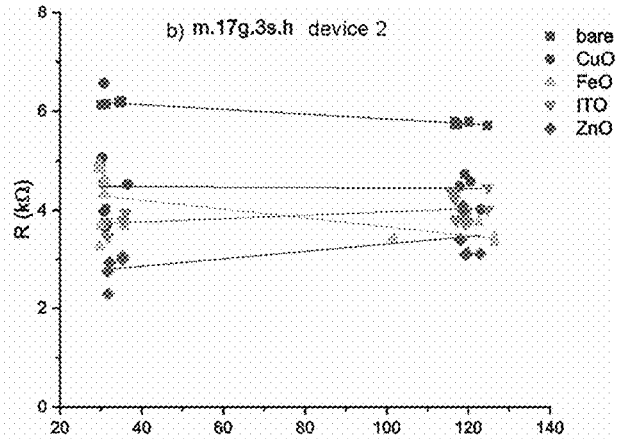
Figure 16C:
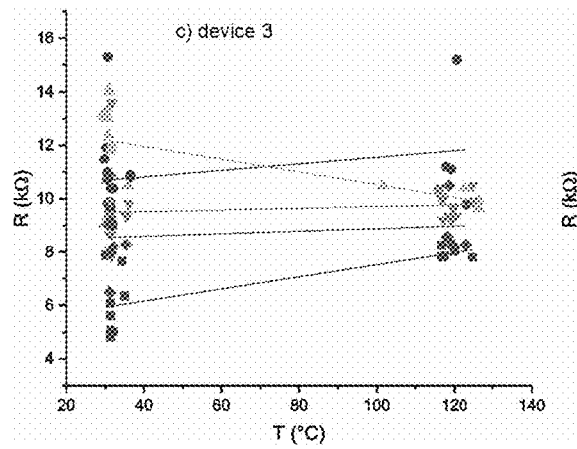
Figure 16D:
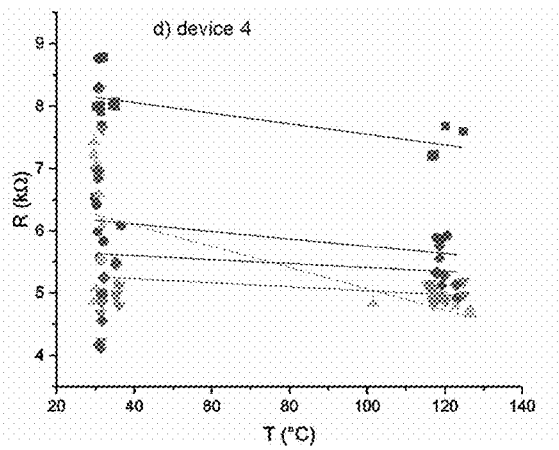

The magnitude of the response of the ITO-graphene sensors was analyzed at the end of the fast response (approximately 10 seconds) and at the end of the slow response (approximately 30 seconds). The results are summarized in FIG. 15. The highest difference in the response between 10 seconds and 30 seconds was detected for JP 8 with 600 ppm. In fact the signal in the first 10 seconds between JP8 with 20 ppm and 600 ppm was identical and only after 30 seconds we could differentiate between the compounds. However, 10 seconds were sufficient to detect and differentiate between sulfur containing S8 mixtures and pure S8.

Sensor Stability

FIG. 16 shows resistances of bare and functionalized devices in all four devices geometries prior to each experiment in an ambient of pure $N_2$ at two temperatures (30° C.,

TABLE 2

Summary of device response in the second series of testing

Room temperature experiments

| Chem | graphene | | | | Gr + ITO | | | | Gr + CuO | | | | Gr + FeO | | | | Gr + ZnO | | | |
|---|---|---|---|---|---|---|---|---|---|---|---|---|---|---|---|---|---|---|---|---|
| | D1 | D2 | D3 | D4 | D1 | D2 | D3 | D4 | D1 | D2 | D3 | D4 | D1 | D2 | D3 | D4 | D1 | D2 | D3 | D4 |
| S8 | + | N | N | + | N | N | N | N | N | N | N | N | N | N | N | N | Not tested | | | |
| S8 + 8T | + | + | N | N | + | + | N | N | + | + | N | + | + | + | N | N | + | + | + | + |
| S8 + Th | + | + | N | – | + | – | N | N | + | N | N | N | + | + | N | N | + | + | N | N |
| S8 + bzT | N | – | N | – | + | + | N | N | + | + | N | + | + | + | + | N | + | + | N | N |
| JP8 20 | | | | | | | | | Not tested | | | | | | | | | | | |
| JP8 600 | | | | | | | | | Not tested | | | | | | | | | | | |

High temperature experiments

| Chem | graphene | | | | Gr + ITO | | | | Gr + CuO | | | | Gr + $Fe_2O_3$ | | | | Gr + ZnO | | | |
|---|---|---|---|---|---|---|---|---|---|---|---|---|---|---|---|---|---|---|---|---|
| | D1 | D2 | D3 | D4 | D1 | D2 | D3 | D4 | D1 | D2 | D3 | D4 | D1 | D2 | D3 | D4 | D1 | D2 | D3 | D4 |
| S8 | N | N | N | N | + | + | N | + | + | + | + | N | N | – | + | N | + | N | N | N |
| S8 + 8T | Not tested | | | | + | + | N | N | Not tested | | | | | | | | | | | |
| S8 + Th | Not tested | | | | + | + | N | N | Not tested | | | | | | | | + | – | N | N |
| S8 + bzT | N | N | N | N | + | + | N | + | Not tested | | | | N | + | – | + | + | + | + | + |
| JP8 20 | Not tested | | | | + | + | N | N | Not tested | | | | Not tested | | | | | | | |
| JP8 600 | Not tested | | | | + | + | N | N | Not tested | | | | Not tested | | | | | | | |

N = no response,
+ = positive response,
– = negative response

Sensor Selectivity as a Function of Device Geometry

Figure 13:
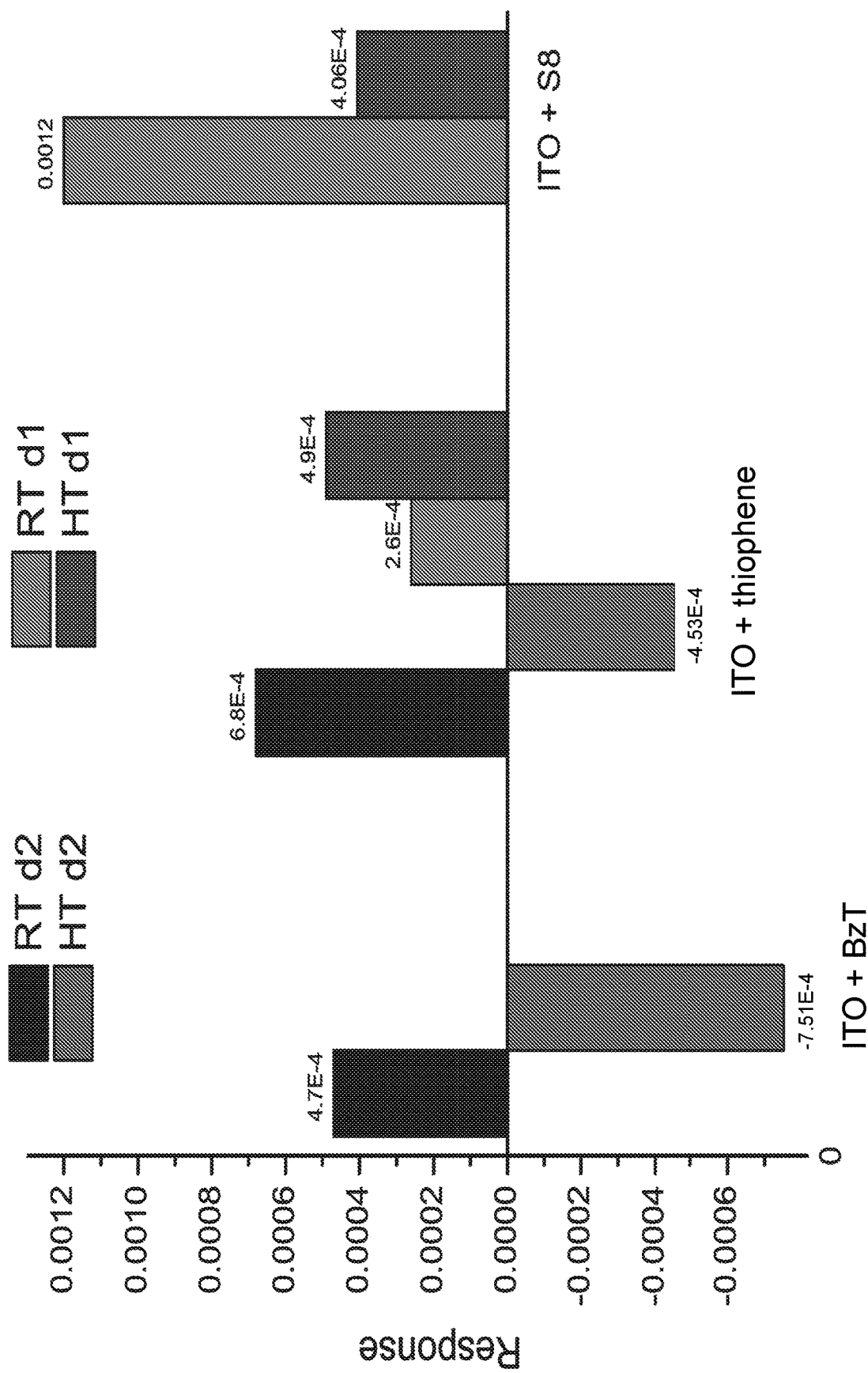
FIG. 13 shows a plot of detector response for ITO functionalized graphene devices with D1 and D2 geometries tested at room (RT) and 130° C. (HT) temperatures. Devices were exposed to pure S8 and S8 mixtures with benzothiophene (BzT) and S8+thiophene. The response is measured as relative conductance change $(G-G_0)/G_0$.
Figure 14:
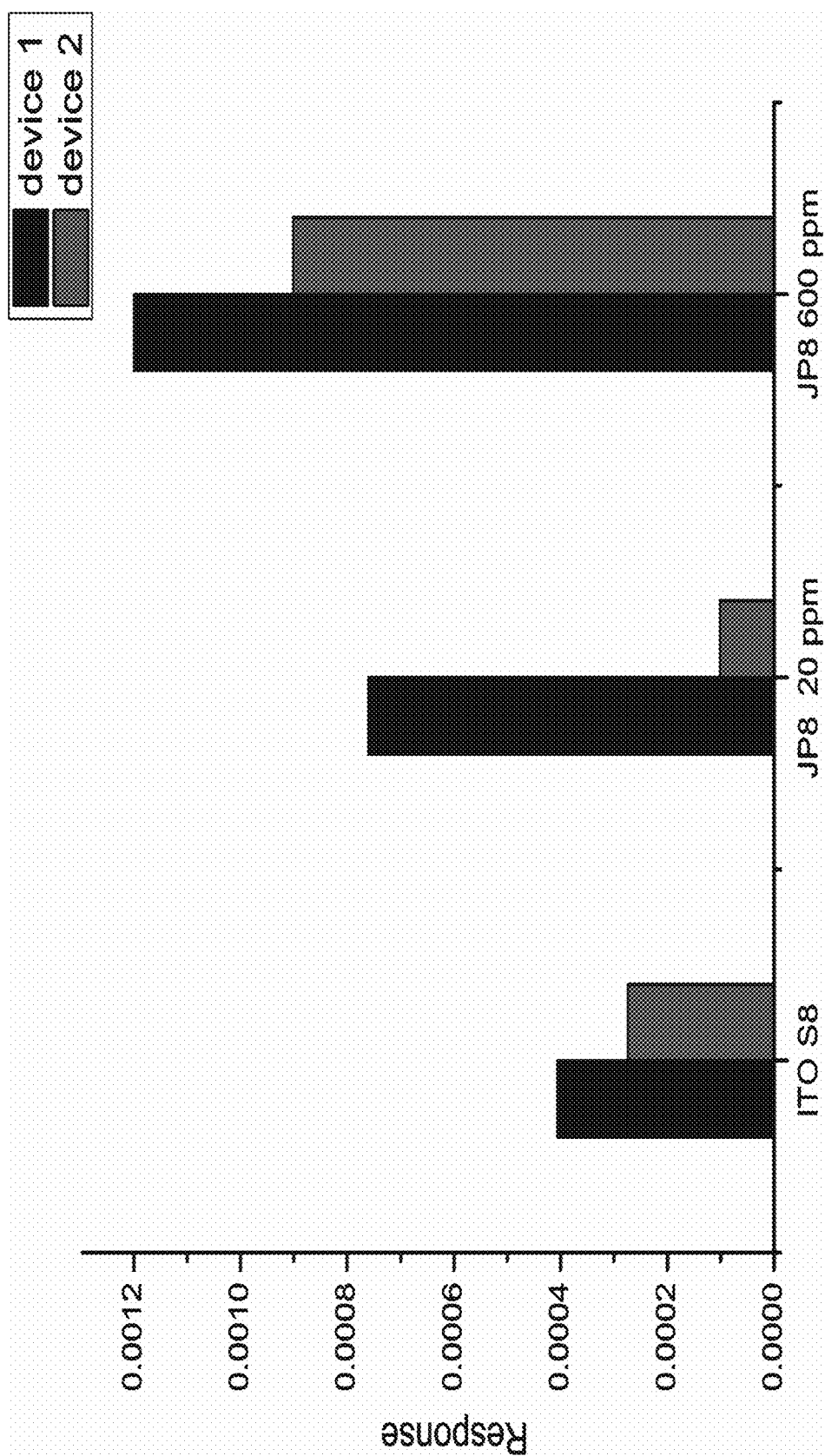
FIG. 14 shows a plot of detector response for ITO functionalized graphene devices with D1 geometries tested at 130° C. temperature. Devices were exposed to pure S8 and aviation fuel JP8 with 20 ppm and 600 ppm sulfur content. The response is measured as relative conductance change $(G-G_0)/G_0$.

A comparison of the responses of devices D1 and D2 at room temperature and at 125° C. is shown in FIG. 13. The change in the performance of ITO-Gr device 2 exposed to S8+BzT and S8+Th was the most striking—signal sign reversal as well as change in magnitude of the response for the above mentioned mixtures was detected. For device 1, there was a factor of two increase of response towards S8+1000 ppm of Th at high temperature, and an almost of magnitude of decrease in response towards pure S8. Furthermore, when the performance of device 1 and 2 was tested at high temperature with pure synthetic fuel S8 with no sulfur and aviation fuels JP8 with 20 ppm and 600 ppm sulfur content, as shown in FIG. 14, the differences were even more apparent. While device 1 had a linear increase in response with increase in sulfur content, the response of device 2 first decreased with sulfur content increase and then 125° C.). Several observations were readily apparent. There was considerable scatter in the measured resistance values at low temperature as compared to the higher temperature. Some of this may be attributable to insufficient recovery between experiments, an effect ameliorated by heating. In general, the higher temperature resistance values were comparable to the lower temperature values, with two exceptions. The most temperature sensitive functionalization was $Fe_2O_3$. Unfunctionalized graphene had the highest resistivity in the case of three of the devices; and a positive temperature coefficient of resistivity, implying a fundamentally different factor dominating charge transport. In later experiments, we tested device performance a year after fabrication and established ppb level of sensitivity in ZnO functionalized graphene devices.

Figure 17A:
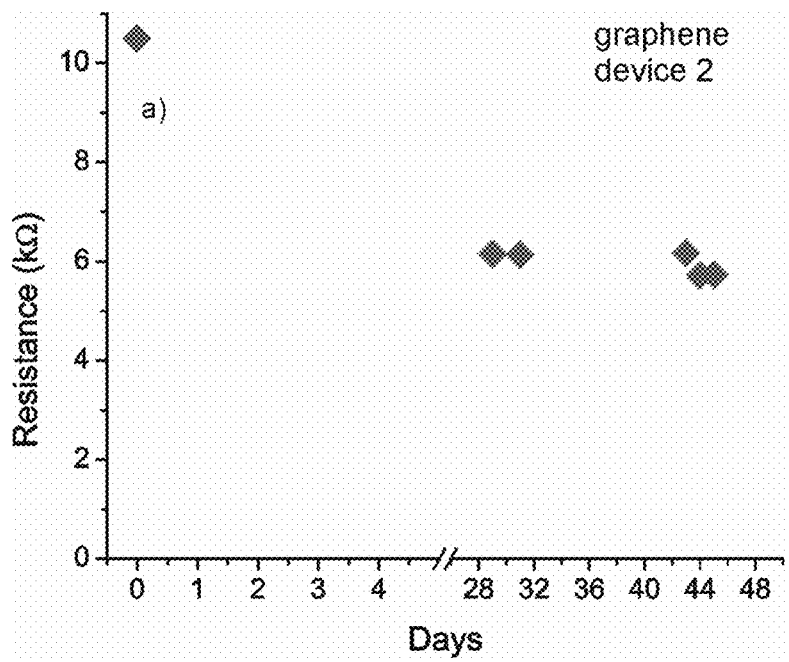
FIG. 17A shows graphene device 2 geometry (horizontally etched graphene)-resistance measurements prior to each experiment.
Figure 17B:
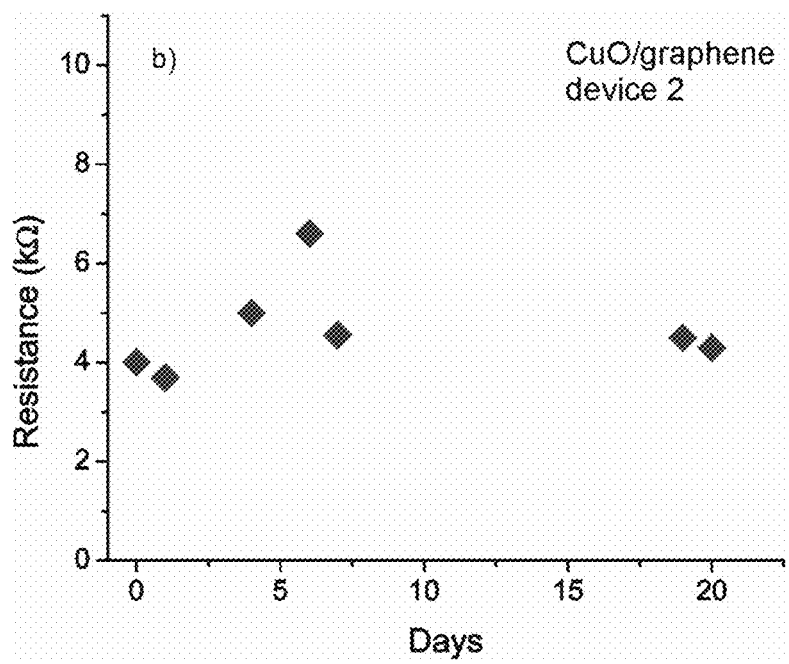
FIG. 17B shows CuO functionalized graphene device 2 geometry (horizontally etched graphene)-resistance measurements prior to each experiment.

FIGS. 17A-B shows the resistance over time for device 2 geometry (horizontally etched graphene) for the bare (FIG.

17A) and CuO functionalized chips (FIG. 17B). Day 0 denotes the resistance before measurements. In case of bare graphene devices heated at 125° C. for 5-30 min before measurements at room temperature (days 29-31) and devices kept at high temperature (days 43-45) had similar resistances of 6 kΩ. It should be noted that when heating was conducted in prior experiments, after the devices were loaded into the testing system, they were allowed to equilibrate to room temperature prior to testing. For CuO-graphene device 2 the resistance before exposure (day 0) is around 4 kΩ. The devices were sitting in $N_2$ stream without additional heating (day 1, 6), when the largest variations were observed. While when the devices were heated at 125° C. for 5-15 minutes before measurements (days 4, 7, 19) and when the devices were measured at high temperature (day 20), a resistance of 5 kΩ) was measured. It should be noted that each device geometry has different resistance values and variation. However, the general trend is that device heating enables constant starting conditions prior exposure to fuel.

Bare graphene and four nanoparticle functionalized (CuO, $Fe_2O_3$, ITO and ZnO) devices were exposed to pure synthetic fuel, mixtures of synthetic fuels and sulfur containing compounds and JP8 fuels with different sulfur content. Four different device geometries at room and elevated temperatures were tested. The major findings are outlined below:

Testing five different chips allows for differentiation of sulfur containing compounds.

ITO/graphene functionalized device gave the strongest response.

ITO functionalized devices in device 1 geometry tested at 125° C. had higher signal for JP8 600 ppm fuel compared to JP8 20 ppm fuel. However, it was hard to definitely establish whether the device was reacting only to sulfur content or to other fuel components.

Response varies as a function of device type—devices with etched geometries gave the best results.

Response time varies as a function of temperature—response time at room temperature was 30 seconds, at 125° C.-10 seconds was sufficient.

Sensor response varies with temperature—at room temperature we had slow uptake and slow signal decay, at 125° C. we observed fast uptake, followed by slow uptake and then fast decay, followed by slow signal decay which is indicative to different adsorbate kinetics.

Heating of the chips prior exposure or testing at high temperature allows for device recovery and for establishing consistent starting conditions.

Calculated power consumption was in the microwatt range.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed as new and desired to be protected by Letters Patent of the United States is:

1. A method for ppb level in-line detection of sulfur in fuel, comprising:
    etching graphene;
    functionalizing the etched graphene and attaching metal oxide nanoparticles to the functionalized graphene to form a device, wherein said functionalizing the etched graphene and attaching metal oxide nanoparticles to the functionalized graphene comprises UV-activated chemical functionalization of graphene and attachment of metal oxide nanoparticles through a chemical linking molecule;
    exposing the device to a fuel in the gas or liquid phase;
    detecting a change in conductivity when sulfur is present in the fuel; and
    recovering the device for future use.

2. The method of claim 1, wherein the chemical linking molecule comprises N-ethylamino-4-azidotetrafluorobenzoate (TFPA-$NH_2$).

3. The method of claim 1, wherein the metal oxide nanoparticles comprise ZnO, CuO, indium tin oxide, $Fe_2O_3$, or any combination thereof.

4. The method of claim 1, wherein the graphene is etched to form a mesa structure comprising horizontal or vertical strips.

5. The method of claim 1, wherein recovering the device comprises rinsing the device with isopropanol.

6. The method of claim 1, wherein recovering the device comprises heating the device.

7. A ppb level in-line sulfur detector for gas and liquid phase fuels, made by the method comprising:
    etching graphene, and
    functionalizing the etched graphene and attaching metal oxide nanoparticles to the functionalized graphene to form a device, wherein said functionalizing the etched graphene and attaching metal oxide nanoparticles to the functionalized graphene comprises UV-activated chemical functionalization of graphene and attachment of metal oxide nanoparticles through a chemical linking molecule;
    wherein when the device is exposed to a fuel in a gas or liquid phase, a change in conductivity is detected when sulfur is present in the fuel, and wherein the device can be recovered for future use.

8. The detector of claim 7, wherein the chemical linking molecule comprises N-ethylamino-4-azidotetrafluorobenzoate (TFPA-$NH_2$).

9. The detector of claim 7, wherein the metal oxide nanoparticles comprise ZnO, CuO, indium tin oxide, $Fe_2O_3$, or any combination thereof.

10. The detector of claim 7, wherein the graphene is etched to form a mesa structure comprising horizontal or vertical strips.

11. The detector of claim 7, wherein recovering the device comprises rinsing the device with isopropanol.

12. The detector of claim 7, wherein recovering the device comprises heating the device.

* * * * *